US 9,358,366 B2

(12) United States Patent
Kyvik et al.

(10) Patent No.: US 9,358,366 B2
(45) Date of Patent: Jun. 7, 2016

(54) OFFSET CATHETER SECUREMENT DEVICE

(71) Applicant: TIDI Securement Products, LLC, Neenah, WI (US)

(72) Inventors: Kurt Kyvik, Satellite Beach, FL (US); Arthur Parkhurst, Ocala, FL (US); Brian William Tait, St. Augustine, FL (US)

(73) Assignee: TIDI Securement Products, LLC, Neenah, WI (US)

( * ) Notice: Subject to any disclaimer, the term of this patent is extended or adjusted under 35 U.S.C. 154(b) by 50 days.

(21) Appl. No.: 14/209,113

(22) Filed: Mar. 13, 2014

(65) Prior Publication Data

US 2015/0258309 A1    Sep. 17, 2015

(51) Int. Cl.
*A61M 25/02* (2006.01)
*A61F 13/00* (2006.01)

(52) U.S. Cl.
CPC ...... *A61M 25/02* (2013.01); *A61F 2013/00412* (2013.01); *A61M 2025/0253* (2013.01); *A61M 2025/0266* (2013.01)

(58) Field of Classification Search
CPC ............... A61M 25/02; A61M 2025/0246; A61M 2025/0253; A61M 2025/0266; A61M 2025/026; A61F 2013/00412
USPC .......................................................... 604/180
See application file for complete search history.

(56) References Cited

U.S. PATENT DOCUMENTS

| | | |
|---|---|---|
| 3,138,158 A | 6/1964 | Gordon et al. |
| 3,167,072 A | 1/1965 | Stone et al. |
| 3,828,254 A | 8/1974 | Burgett et al. |
| 3,834,380 A | 9/1974 | Boyd |
| 3,918,446 A | 11/1975 | Buttaravoli |
| 3,973,565 A | 8/1976 | Steer |
| 4,129,128 A | 12/1978 | McFarlane |
| 4,250,880 A | 2/1981 | Gordon |
| 4,460,356 A | 7/1984 | Moseley |
| 4,490,141 A | 12/1984 | Lacko et al. |
| 4,519,793 A | 5/1985 | Galindo |
| 4,699,616 A | 10/1987 | Nowak et al. |
| 4,717,385 A | 1/1988 | Cameron et al. |
| 4,767,411 A | 8/1988 | Edmunds |
| 4,822,342 A | 4/1989 | Brawner |
| 4,838,868 A | 6/1989 | Forgar et al. |
| 4,863,432 A | 9/1989 | Kvalo |
| 4,874,380 A | 10/1989 | Hesketh |

(Continued)

FOREIGN PATENT DOCUMENTS

| CN | 203123273 | 8/2013 |
|---|---|---|
| DE | 20020326 U1 | 2/2001 |

(Continued)

*Primary Examiner* — Kevin C Sirmons
*Assistant Examiner* — Amber Stiles
(74) *Attorney, Agent, or Firm* — Boyle Fredrickson, S.C.

(57) ABSTRACT

A catheter securement device adapted to be adhesively mounted to the skin of a patient to secure a catheter in place, the device having a flexible, thin, sheet-like base member with a distal edge and a midportion, and a releasable, flexible, thin, sheet-like retention member comprising a fixed end, a releasable end, a and a distal edge, wherein the distal edge of the retention member is offset from the distal edge of the base member to define an uplift focus area in the midportion of the base member, such that upward pull on the catheter is transferred to the midportion of the base member to preclude the base member from being peeled from the patient's skin.

19 Claims, 4 Drawing Sheets

(56) References Cited

U.S. PATENT DOCUMENTS

| | | | |
|---|---|---|---|
| 4,915,694 | A | 4/1990 | Yamamoto et al. |
| 5,037,397 | A | 8/1991 | Kalk et al. |
| 5,147,322 | A * | 9/1992 | Bowen et al. ............... 604/180 |
| 5,192,274 | A | 3/1993 | Bierman |
| 5,215,532 | A | 6/1993 | Atkinson |
| 5,219,336 | A | 6/1993 | Wilk |
| 5,224,935 | A | 7/1993 | Hollands |
| 5,232,453 | A | 8/1993 | Plass et al. |
| 5,236,421 | A | 8/1993 | Becher |
| 5,282,791 | A | 2/1994 | Lipton et al. |
| 5,370,627 | A | 12/1994 | Conway |
| 5,380,294 | A | 1/1995 | Persson |
| 5,413,562 | A | 5/1995 | Swauger |
| 5,685,859 | A | 11/1997 | Kornerup |
| 6,273,873 | B1 | 8/2001 | Fleischer |
| 6,419,660 | B1 | 7/2002 | Russo |
| 6,428,516 | B1 | 8/2002 | Bierman |
| D470,936 | S | 2/2003 | Bierman |
| 6,689,104 | B2 | 2/2004 | Bierman |
| D492,411 | S | 6/2004 | Bierman |
| 6,765,122 | B1 | 7/2004 | Stout |
| 6,770,055 | B2 | 8/2004 | Bierman et al. |
| 6,827,705 | B2 | 12/2004 | Bierman |
| 6,837,875 | B1 | 1/2005 | Bierman |
| 6,866,652 | B2 | 3/2005 | Bierman |
| D503,997 | S | 4/2005 | Bierman |
| 6,875,200 | B1 | 4/2005 | Ajagbe |
| 6,929,625 | B2 | 8/2005 | Bierman |
| 6,951,550 | B2 | 10/2005 | Bierman |
| 6,979,320 | B2 | 12/2005 | Bierman |
| 7,018,362 | B2 | 3/2006 | Bierman et al. |
| D528,206 | S | 9/2006 | Bierman |
| 7,137,968 | B1 | 11/2006 | Burrell et al. |
| 7,524,307 | B2 | 4/2009 | Davis et al. |
| 7,637,894 | B2 | 12/2009 | Fleisher |
| D608,444 | S | 1/2010 | Kyvik et al. |
| D608,887 | S | 1/2010 | Kyvik et al. |
| 7,648,485 | B2 | 1/2010 | Fleisher |
| D616,091 | S * | 5/2010 | Kyvik .................. D24/128 |
| D616,542 | S | 5/2010 | Kyvik et al. |
| D616,983 | S | 6/2010 | Kyvik et al. |
| 7,766,880 | B1 | 8/2010 | Spinoza |
| D625,002 | S | 10/2010 | Kyvik et al. |
| 7,812,212 | B2 | 10/2010 | Propp et al. |
| D652,509 | S | 1/2012 | Kyvik et al. |
| 8,128,602 | B2 | 3/2012 | Tollini et al. |
| 8,157,770 | B2 | 4/2012 | Elwell et al. |
| D663,834 | S | 7/2012 | Kyvik et al. |
| 8,241,253 | B2 | 8/2012 | Bracken |
| 8,251,957 | B2 | 8/2012 | Kyvik et al. |
| 8,500,698 | B2 | 8/2013 | Kyvik et al. |
| 8,608,706 | B2 | 12/2013 | Davis et al. |
| 8,834,427 | B2 | 9/2014 | Kyvik et al. |
| D715,927 | S | 10/2014 | Kyvik et al. |
| D715,928 | S | 10/2014 | Kyvik et al. |
| 2002/0195114 | A1 | 12/2002 | Tollini |
| 2008/0200880 | A1* | 8/2008 | Kyvik .................. A61M 25/02 604/180 |
| 2010/0036324 | A1* | 2/2010 | Smith .................. A61M 25/02 604/180 |
| 2010/0298778 | A1 | 11/2010 | Bracken |
| 2011/0021997 | A1 | 1/2011 | Kyvik et al. |
| 2012/0316504 | A1 | 12/2012 | Kyvik et al. |
| 2013/0096507 | A1 | 4/2013 | Lelievre |
| 2013/0150796 | A1 | 6/2013 | Souza et al. |

FOREIGN PATENT DOCUMENTS

| | | |
|---|---|---|
| EP | 0408389 | 1/1991 |
| GB | 2464662 A | 4/2010 |

* cited by examiner

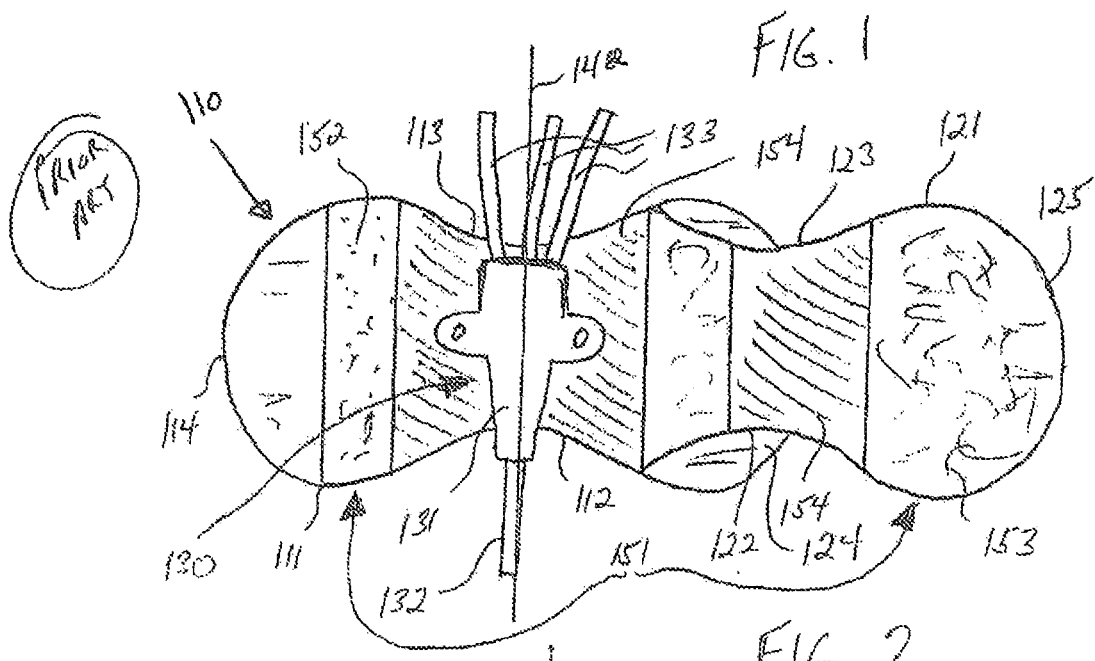
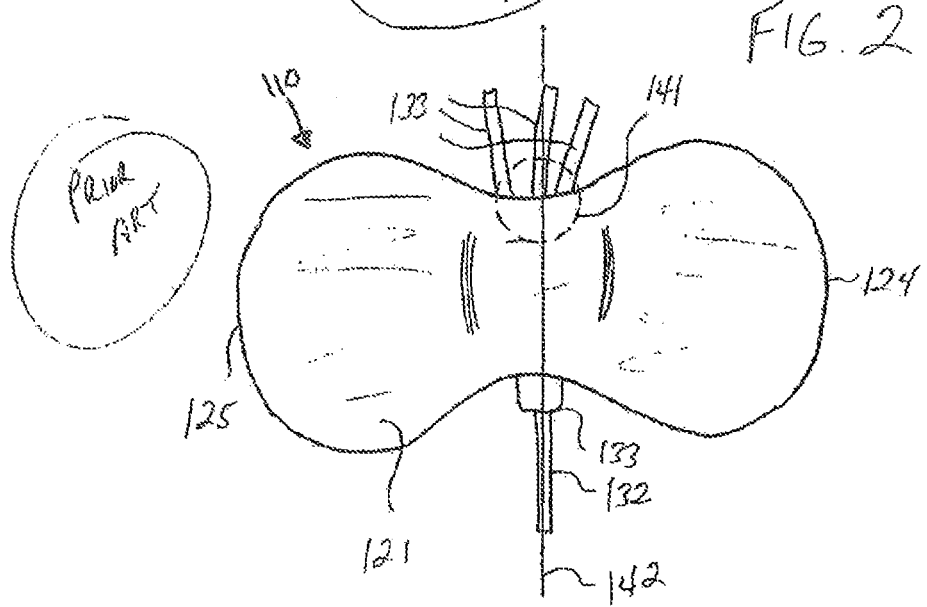

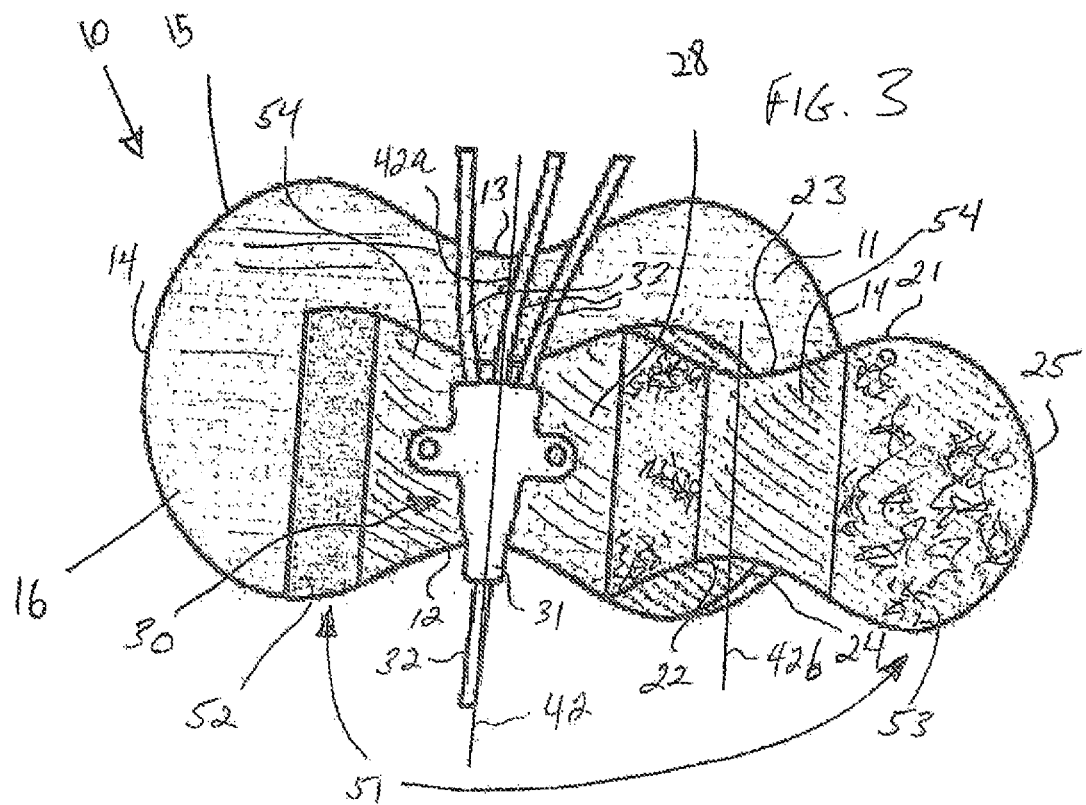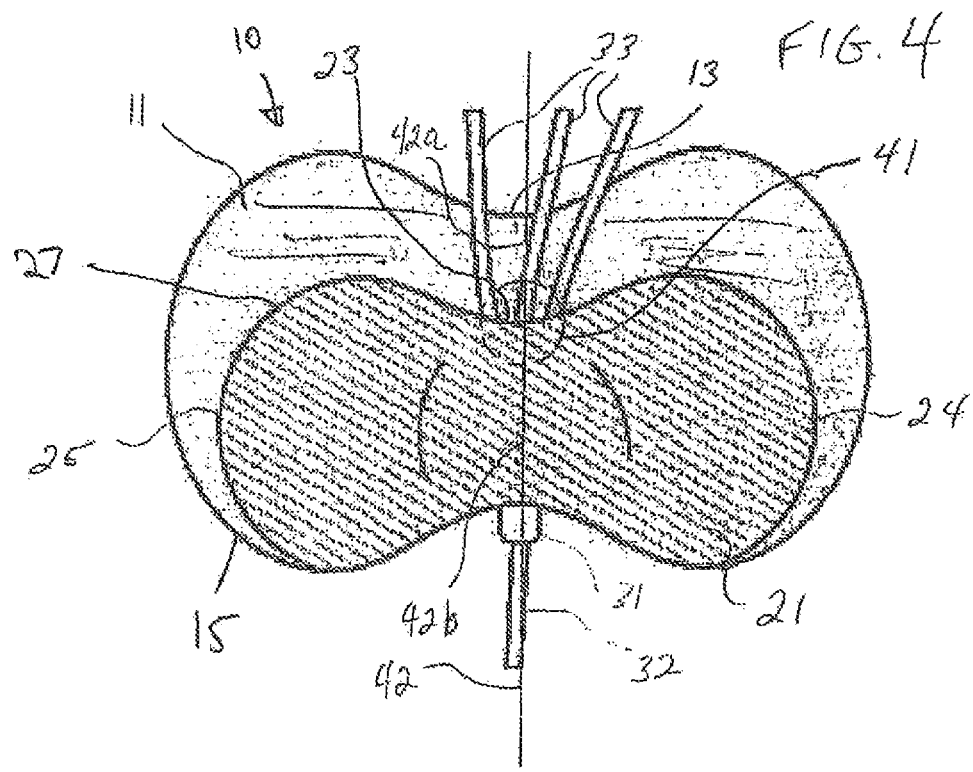

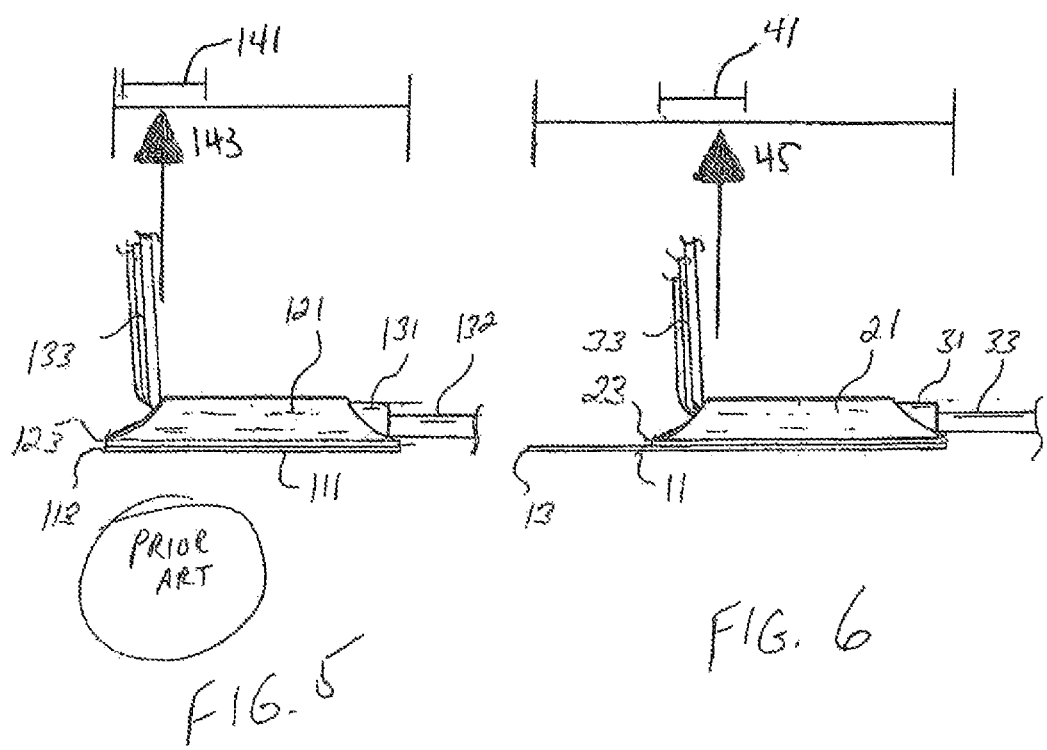

OFFSET CATHETER SECUREMENT DEVICE

BACKGROUND OF THE INVENTION

This invention relates generally to the field of medical devices referred to as catheter securement devices, a catheter being defined herein to include or comprise a small diameter, flexible tube that is inserted through a person's skin and into a vein to deliver or remove fluids such as blood, saline solutions, medications, etc., and often comprising a catheter hub or housing acting as a coupling member such that multiple distal tubes may be in fluid communication with the single tube leading from the insertion site. The catheter housing may also be utilized in order to provide a larger body for easier securement even if a single distal conduit tube is present. A catheter securement device typically comprises a flexible sheet member adhesively adhered to the patient's skin, the device having a clamp, flap or strap member to restrain and secure the catheter tubing or a catheter housing in a relatively stable manner such that it is less likely for the catheter to be accidentally pulled from the patient. The catheter tubing or housing may be secured within the securement device by pressure, adhesive, recessed members, etc.

Catheter securement devices are typically located a short distance away from the insertion, such that the length of the proximal portion of the catheter tubing is relatively short. The distal catheter tube or tubes to the contrary may be relatively long. A problem encountered with catheter securement devices of known design is that any lifting force applied intentionally or accidentally to the distal conduit tubes, i.e., the tubes extending beyond the catheter hub on the opposite side of the catheter securement device from the proximal conduit tube leading to the insertion site, may result in undesirable edge uplift force on the catheter securement device, causing the catheter securement device to be pulled or peeled from the patient's skin with possible dislodgement of the catheter.

It is an object of this invention to provide a catheter securement device that reduces the likelihood of accidental dislodgement of the catheter securement device by providing a structural design that shifts the upward force focus of any uplift force, created by pulling the distal tube or tubes in a direction generally perpendicular to the skin surface, to a location away from the edge and into the mid-portion of the catheter securement device, and in particular away from the distal edge and into the mid-portion of the base member adhered to the patient's skin.

SUMMARY OF THE INVENTION

The invention is a catheter securement device adapted to be adhesively adhered to the skin of a patient, the device comprising a flexible, thin, sheet-like base member, a lower adhesive layer being disposed on the underside of the base member, and a releasable, thin, flexible sheet, flap or strap catheter retention member mounted to the upper side of the base member, the releasable retention member having a fixed end and a releasable free end. The securement device has a centralized transverse midline located where the catheter tube or housing is positioned during use, the tube or housing being aligned such that the transverse midline of the base member and the retention members are generally vertically aligned with the axis defined by the catheter. A releasable fastening mechanism is provided, such as a pressure-sensitive adhesive, a hook-and-loop mechanism or the like, in order to securely fasten the retention member onto the base member once positioned across the catheter to preclude the catheter from undesired movement. The retention member and base member are arranged such that the retention member overlays the base member in an offset manner such that the distal edge of the retention member on the transverse midline is located over the midportion of the base member, i.e., the base member extends farther in the distal direction than at least a portion of the retention member.

The base member is preferably structured to have a midline longitudinal dimension greater than its midline transverse dimension, and also preferably is provided with a "dog-bone" or "bowtie" configuration such that the transverse width of the base member adjacent both sides of the transverse midline increases progressively away from the transverse midline to a point where the ends of the base member are rounded. Preferably, the retention member is likewise configured, but smaller overall. The transverse midline width of the retention member is smaller than the transverse midline width of the base member and the retention member is attached in offset manner relative to the base member, such that the distal edge of the retention member is located in the midportion or interior of the base member along the transverse midline. This offset defines a center of uplift or an uplift focus area in the midportion of the base member, whereby pulling the distal tubes results in a 360 degree spreading or dispersal of the uplift force radiating throughout the base member rather than a concentrated edge uplift force as found in conventional catheter securement devices.

While the "dog bone" configuration has been found to be beneficial in properly dispersing the upward forces, the device may have varying configurations for the base and retention members as long as the distal edge of the retention member at the transverse midline is located offset from the distal edge of the base member such that the uplift center is located within the midportion of the base member such that force is spread radially about the base member. In this manner, any uplift force applied to the distal tubes results in a "tenting" or "coning" effect rather than a peeling effect on the base member, thereby greatly increasing the sustainable pull force before separation from the patient's skin occurs.

Alternatively summarized, the invention is a catheter securement device adapted to be adhesively mounted to the skin of a patient to secure a catheter comprising a distal tube member, said device comprising a flexible, thin, sheet-like base member comprising a proximal edge, a distal edge and a midportion; a releasable, flexible, thin, sheet-like retention member comprising a fixed end, a releasable end, a proximal edge and a curved distal edge, said fixed end attached to said base member and said releasable end releasably attached to said base member; wherein said curved distal edge of said retention member is offset from said distal edge of said base member such that said distal edge of said retention member defines an uplift focus area located in the middle 50% of said midportion of said base member. The device may further comprise a transverse midline, wherein said distal edge of said retention member is offset from said distal edge of said base member at said transverse midline, and wherein said transverse midline is laterally centered on said base member, and/or wherein said retention member is smaller than said base member and wherein said base member and said retention member are dog-bone shaped.

Alternatively still the invention may be characterized as the combination of a catheter securement device adapted to be adhesively mounted to the skin of a patient and a catheter comprising a distal tube member, said combination comprising a flexible, thin, sheet-like base member comprising a proximal edge, a distal edge and a midportion; a releasable, flexible, thin, sheet-like retention member comprising a fixed end, a releasable end, a proximal edge and a distal edge, said fixed end attached to said base member and said releasable end releasably attached to said base member, wherein said retention member is releasably securable across said catheter when said catheter is disposed on said base member such that a portion of said distal edge of said retention member extends across said distal tube member, said portion of said distal edge of said retention member being offset from said distal edge of said base member; wherein said portion of said distal edge of said retention member extending across said distal tube member is offset from said distal edge of said base member, whereby said distal tube members are restrained by said portion of said distal edge of said distal tube member when upward force is applied to said distal tube members such that an uplift focus area is defined by said portion of said distal end of retention member, said uplift focus are being located in said midportion of said base member. The combination may be characterized such that said distal edge of said retention member is curved, said retention member is smaller than said base member, said base member and said retention member are dog-bone shaped, wherein the location of said catheter on said base member defines a transverse midline, and wherein said uplift focus area is located on said transverse midline, and/or wherein said uplift focus area is located in the middle 50% of said base member.

BRIEF DESCRIPTION OF THE DRAWINGS

FIG. 1 is a prior art catheter securement device, shown in the open position.

FIG. 2 is the prior art catheter device of FIG. 1, shown in the closed position securing a catheter.

FIG. 3 is an embodiment of the offset catheter securement device of this invention, shown in the open position.

FIG. 4 is the offset catheter securement device of FIG. 3, shown in the closed position securing a catheter.

FIG. 5 is a longitudinal view of the prior art catheter device of FIG. 2, illustrating the uplift force as concentrated on the edge of the base member.

FIG. 6 is a longitudinal view of the embodiment of FIG. 4, illustrating the uplift force as concentrated in the midportion of the base member.

DETAILED DESCRIPTION OF THE INVENTION

With reference to the drawings, the invention will now be described in detail with regard for the best mode and the preferred embodiment. In general, the invention is a catheter securement device that adheres to the skin of a patient having an epidural catheter or similar small flexible tube member inserted percutaneously, the securement device acting to secure and restrain the catheter tube or housing to prevent or reduce movement near the insertion site or accidental dislodgement of the catheter. The securement device in general comprises a flexible, thin, sheet-like base member capable of adhering to the skin of the patient and a releasable flexible, thin, sheet-like retention member to secure the catheter onto the main body member, the retention member being mounted onto the base member in an offset manner.

As used herein, the term "catheter" shall include a tube member alone or multiple tubes in combination with a catheter hub or housing member. The term "proximal" shall refer to the direction from the catheter securement device toward the catheter insertion site and the term "distal" shall refer to the direction away from the catheter securement device opposite from the insertion site, such that for example the term "proximal tube" shall refer to the tube extending between the insertion site and the securement site and the term "distal tube" shall refer to a tube extending from the securement device on the side opposite that of the insertion site. The term "proximal edge" shall refer to the side of the catheter securement device facing toward the insertion site and the term "distal edge" shall refer to the side of the securement device facing away from the insertion site. The position of the catheter relative to the securement device when the device is in use shall generally define the "axis" or the "axial direction" of the catheter, with the term "transverse" defining the direction generally parallel to the axial direction, i.e., the width of the device, and the term "longitudinal" defining the direction perpendicular to the transverse direction. The term "transverse midline" shall define a line located generally parallel to and in approximate vertical alignment with the catheter axis when the device is in use, which is preferably located as the true dimensionally-centered midline of the base member and retention member. The terms "midportion" or "interior" shall refer to a location away from the outer edges of the base member. The term "uplift focus area" shall refer to a point or small area where uplift forces resulting from pulling a distal tube in the direction perpendicular (i.e., vertical) to the skin of the patient are initially concentrated on or transferred to the base member of the catheter securement device.

Figure 7:
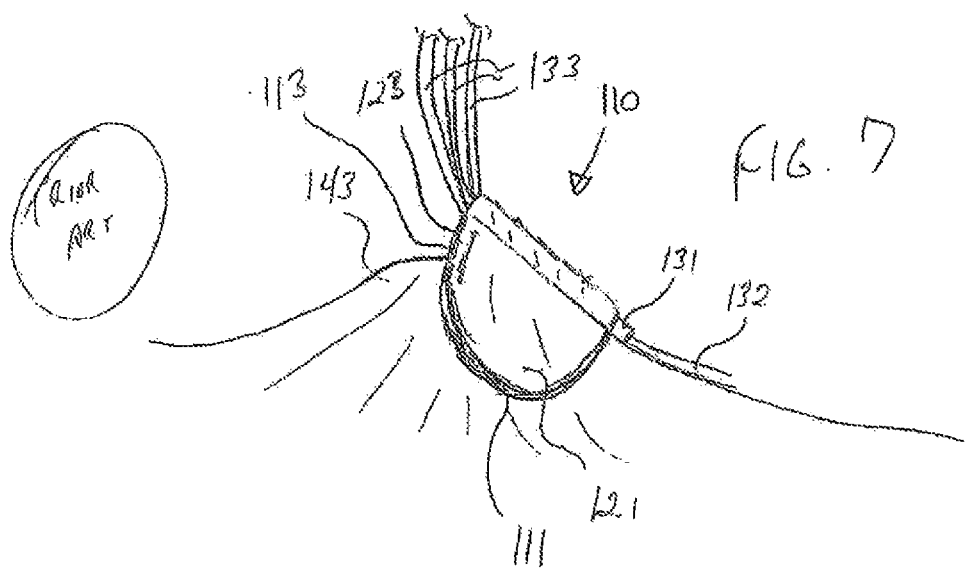
FIG. 7 is a longitudinal view of the prior art catheter device of FIG. 2, illustrating the uplift force as concentrated on the edge of the base member, resulting in a peeling effect such that the base member is separated from the patient's skin.

An exemplary embodiment of prior art catheter securement devices 110 is illustrated in FIGS. 1, 2, 5 and 7, which show a catheter securement device 110 comprising a base member 111 and a releasable retention member 121. The base member 111 is a flexible, thin, sheet-like member, having an adhesive backing and generally elongated preferably into a "dog bone" configuration with a proximal edge 112 and a distal edge 113, both of which are preferably concave, and two ends 114, preferably rounded, the base member 111 and retention member 112 being shorter in transverse direction than in the longitudinal direction. The retention member 121 is a flexible, thin, sheet-like strap or flap member having a fixed end 124 secured to the base member 111 and a free end 125, also shown in a "dog bone" configuration with a concave proximal edge 122 and distal edge 123. A releasable fastening mechanism or system 151 is present, as shown comprising a hook component 152 and a loop component 153 of a suitable hook-and-loop fastener. An optional adhesive layer 154 may be provided as shown on the upper surface of the base member 111 and/or the underside of the retention member to better secure the catheter 130. As shown in the figures, the catheter 130 is embodied as a housing or hub 131 with a proximal (insertion) tube member 132 and multiple distal (accessory connecting) tube members 133. The transverse midline 142 is illustrated as being laterally centered. An uplift focus area 141 occurs at the point or area at or near the distal edge 123 of the retention member, depending on the tautness of the retention member 121 relative to the base member 111, where uplift forces 143 are applied to distal tube members 133. Because the transverse width of the base member 111 is substantially equal with that of the retention member 112, the distal edges 113 and 123 at the transverse midline 142 are aligned. This results in the uplift focus area 141 occurring at or adjacent the distal edge 113 of the base member 111 as well, as shown in FIGS. 2 and 5, thereby leading to lifting of the distal edge 113 when uplift forces 143 are applied, to the distal tube members 133, as shown in FIG. 7, such that a peeling effect is created and the base member 111 is susceptible to being peeled from the patient's skin 143.

Figure 8:
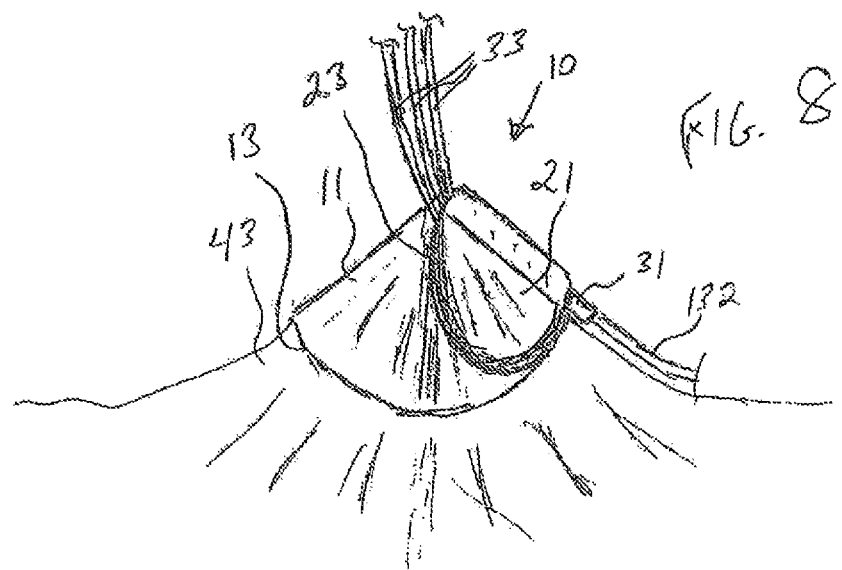
FIG. 8 is a longitudinal view of the prior art catheter device of FIG. 4, illustrating the uplift force as concentrated in the midportion of the base member, resulting in a tenting effect such that the base member is not separated from the patient's skin.

The invention addresses this problem, as shown in the illustrated embodiment of FIGS. 4, 6 and 8, by providing an improved catheter securement device 10 for securing a catheter 30 comprising as shown a catheter housing 31, a proximal tube member 32 and plural distal tube members 33 to a patient's skin 43. As illustrated, the catheter securement device 10 is adapted to be adhesively adhered to the skin 43 of a patient, the device comprising a thin, flexible, sheet-like base member 11 with an upper side 16 and an underside 17, a lower adhesive layer 54 being disposed in known manner on the underside 17 of the base member 11 to adhere the base member 11 directly to the patient's skin 43, and a releasable, thin, flexible, sheet-like catheter retention member 21, in the form of a flap or strap, mounted to the upper side 16 of the base member 11, the releasable retention member 21 having a fixed end 24 and a releasable free end 25. Alternatively, but not preferred, both ends of the retention member 21 could be releasable affixed to the base member 11. The fixed end 24 is secured to the upper side 16 of the base member 11 in suitable known manner, such as by adhesive bonding, stitching, melt bonding, hook-and-loop fastener, or the like. A releasable fastening mechanism or system Si is provided, such as a pressure-sensitive adhesive, a hook-and-loop mechanism, or the like, in order to securely retain the retention member 21 onto the base member 11 when the retention member 21 is pulled tautly across the catheter 30 to preclude the catheter 30 from undesired movement. As shown in this embodiment, the releasable fastening mechanism 51 is a hook-and-loop fastener comprising the releasable combination of a hook component 52 and a loop component 53.

The base member 11 comprises a proximal edge 12, a distal edge 13, a pair of ends 14 and a transverse midline 42a (most preferably centered laterally). The base member 11 has a perimeter 15 defined by the proximal edge 12, the distal edge 13, and the pair of ends 14. The retention member 21 comprises a proximal edge 22, a distal edge 23 and a transverse midline 42b, such that the transverse midlines 42a and 42b overlap so as to be generally vertically aligned when the retention member 21 is closed over the catheter 30 and secured to the base member 11. The retention member 21 also has a perimeter 27 defined by the proximal edge 22, the distal edge 23, the free end 25 and the fixed end 24. As can be seen, for instance in FIG. 4, the perimeter 15 of the base member 11 is greater perimeter 27 of the retention member 21. The distal edge 23 of the retention member 21 is positioned offset from the distal edge 13 of the base member 11, preferably over the entire longitudinal length of the securement device 10 but at least in the area corresponding to the position of the distal tube members 33, i.e., in the area of the transverse midline 42 defined by the position of the catheter 30. The transverse midline 42 is located and defined by the location of the axis of the catheter 31 during use, the securement device and catheter 31 being positioned such that the transverse midline 42a of the base member and the transverse midline 42b of the retention members are generally vertically aligned with the main transverse midline 42 defined by the position of the catheter 31 axis when the retention member 21 is fastened across the catheter 30. Preferably, the retention member 21 and base member 11 are sized and arranged such that the smaller retention member 21 overlays the larger base member 21 in an offset manner such that at least a portion of the distal edge 23 of the retention member 21 on the transverse midline 42 is located over the midportion 28 or interior of the base member 11 and is separated away from the distal edge 13 of the base member 11, such that the distal edge 13 of the base member 11 extends farther in the distal direction than the retention member 21.

The base member 11 is preferably structured to have a midline longitudinal dimension greater than its midline transverse dimension, and also preferably is provided with a "dogbone" or "bowtie" configuration such that the transverse width of the base member 11 adjacent both sides of the transverse midline 42a increases progressively away from the transverse midline 42a to a point where the ends 14 of the base member 11 are rounded, thereby producing concave proximal and distal edges 22/23. Preferably, the retention member 21 is likewise configured, but smaller overall. Other configurations for the perimeters 15 of the base member 11 and the perimeter 27 of the retention member 21 are also possible. Alternatively for example, a short segment of the distal edge 23 of the retention member 21 over and adjacent the transverse midline 42b, i.e., the segment that resides over the distal tube members 33 when in use, may be recessed, notched or indented while the remaining portions of the distal edge 23 extend toward or to the distal edge 13 of the base member 11.

The location of the distal edge 23 of the retention member 21 in the area of the transverse midline 42b defines an uplift focus area 41 representing the focus of uplift forces 45 when the distal tube members 33 are pulled generally perpendicularly away from the securement device 10 and the skin 43 of the patient. The uplift force 45 on the distal tube members 33 is intercepted and restricted by the distal edge 23 of the retention member 21, such that the uplift force 45 is transmitted down to the base member 11 and the patient's skin 43 at this uplift focus area 41. In prior art devices wherein the distal edge 123 of the retention member 121 is adjacent or overlaps the distal edge 113 of the base member 111, as shown in FIGS. 5 and 7, the uplift focus area 141 is situated at or adjacent the distal edge 113 of the base member 111. In this circumstance, when the distal tube members 133 are pulled upward, the uplift force 143 becomes an edge uplift force 143 concentrated on the distal edge 113 which produces a peeling effect. If the edge uplift force 143 exceeds the base member adhesive force, the base member 111 will be peeled from the patient's skin 143.

By offsetting the retention member distal edge 23 from the base member distal edge 13, the uplift focus area 41 is shifted into the midportion 28 or interior of the base member 11, whereby pulling the distal tube members 33 results in a 360 degree dispersion of the uplift force 45 across and within the base member 11, as shown in FIGS. 6 and 8. With this construction, the uplift force 45 produces a tenting or coning effect on the base member 11 and the underlying skin 43, such that the likelihood of de-adhesion of the base member 11 is greatly reduced, since a much greater force 45 is required to separate the base member 11 away from the skin 43 in the interior of the base member 11 than is required to peel the base member 11 from the skin by its edge.

As discussed above, while the "dog bone" configuration has been found to produce excellent results in practice, the device could have varying configurations for the base member 11 and retention member 21 as long as the distal edge 23 of the retention member 21 at the transverse midline 42 is located offset from the distal edge 13 of the base member 11 such that the uplift focus area 41 is located within the midportion 28 of the base member 11 such that uplift force 45 is radially dispersed about the midportion of the base member 11. In this manner, any uplift force 45 applied to the distal tube members 31 results in a "tenting" or "coning" effect rather than a peeling effect of the base member 11, thereby greatly increasing the sustainable pull force before separation from the patient's skin 43 occurs.

While particular dimensions may vary, it is preferred that the elements of the device be configured and sized such that the uplift focus area 41 is centered along the transverse midline 42 in the middle 50% of the base member 11, i.e., for a base member 11 having a two inch width on the transverse midline 42, the retention member distal edge 23 on the transverse midline 42 is situated between about one quarter inch to about three quarter inches from the base member distal edge 13. More preferably, the uplift focus area 41 is more centrally located, such that for the two inch wide example given above the retention member distal edge 23 is situated between about one quarter inch to about one half inch from the base member distal edge 13. The more tightly the catheter 31 is secured within the catheter securement device 10, i.e., the more tautly the retention member 21 is secured to the base member 11, the closer the true center of the uplift focus area 41 will be to the distal edge 23 of the retention member 21. For a looser securing, the true center of the uplift focus area 41 will shift slightly away from the distal edge 23.

It is to be understood that equivalents and substitutions to elements and structures set forth above, which are not intended to be limiting unless necessary for patentability, may be obvious to those of ordinary skill in the art, and therefore the true scope and definition of the invention is to be as set forth in the following claims.

We claim:

1. A catheter securement device adapted to be adhesively mounted to the skin of a patient to secure a catheter comprising a distal tube member, said device comprising:
    a flexible, thin, sheet-like base member comprising a proximal edge, a distal edge and a midportion located between said proximal edge and said distal edge of the base member;
    a releasable, flexible, thin, sheet-like retention member comprising a fixed end, a releasable end, a proximal edge and a distal edge, said fixed end attached to said base member and said releasable end releasably attached to said base member, said retention member substantially parallel to said base member when said releasable end is attached to said base member; said distal edge of the retention member located adjacent to the midportion of the base member when the releasable end is attached to said base member;
    wherein said distal edge of said retention member is laterally offset from said distal edge of said base member; and
    wherein said retention member is configured to form an uplift focus area located at said midportion of the base member when upward force is applied to said distal tube member such that said base member tents up when the upward force is applied to the distal tube member.

2. The device of claim 1, further comprising a transverse midline, wherein said distal edge of said retention member is offset from said distal edge of said base member at said transverse midline.

3. The device of claim 2, wherein said transverse midline is laterally centered on said base member.

4. The device of claim 1, wherein said uplift focus area is located in the middle 50% of said base member.

5. The device of claim 3, wherein said uplift focus area is located in said midportion of said base member along said transverse midline of said base member.

6. The device of claim 5, wherein said retention member is smaller than said base member.

7. A combination of a catheter securement device adapted to be adhesively mounted to the skin of a patient and a catheter comprising a distal tube member, said combination comprising:
    a flexible, thin, sheet-like base member comprising a proximal edge, a distal edge and a midportion;
    a releasable, flexible, thin, sheet-like retention member comprising a fixed end, a releasable end, a proximal edge and a distal edge, said fixed end attached to said base member and said releasable end releasably attached to said base member, wherein said retention member is releasably securable across said catheter when said catheter is disposed on said base member such that a portion of said distal edge of said retention member extends across said distal tube member, said portion of said distal edge of said retention member being laterally offset from said distal edge of said base member along a horizontal axis extending through a transverse midline of the base member;
    wherein said portion of said distal edge of said retention member extending across said distal tube member is offset from said distal edge of said base member, whereby said distal tube member is restrained by said portion of said distal edge, and whereby said portion of said distal edge of retention member is configured to form an uplift focus area located at said midportion of said base member when upward force is applied to said distal tube member.

8. The combination of claim 7, wherein said distal edge of said retention member is curved.

9. The combination of claim 7, wherein said retention member is smaller than said base member.

10. The combination of claim 9, wherein said base member and said retention member are dog-bone shaped.

11. The combination of claim 7, wherein the location of said catheter on said base member defines a transverse midline, and wherein said uplift focus area is located on said transverse midline.

12. The combination of claim 7, wherein said uplift focus area is located in the middle 50% of said base member.

13. A catheter securement device removably adhered to a patient's skin to secure a catheter housing with a plurality of distal tube members comprising:
    a base member defining a perimeter with an upper side and an underside, the base member comprising a distal edge opposite a proximal edge and a first end opposite a second end;
    a retention member defining a perimeter with a distal edge opposite a proximal edge and a fixed end fixedly attached to the upper side of the base member and a free end releaseably attached to the upper side of the base member, the distal edge of the retention member laterally offset from the distal edge of the base member along the entire length of the distal edge of the retention member and the proximal edge of the retention member flush with the proximal edge of the base member along the length of the proximal edge of the retention member.

14. The catheter securement device of claim 13, wherein the perimeter of the retention member is smaller than the perimeter of the base member.

15. The catheter securement device of claim 14, further comprising an adhesive layer on the upper side of the base member located underneath the retention member configured to receive the catheter housing.

16. The catheter securement device of claim 14, further comprising an uplift focus area where a force applied to the plurality of distal tube members is transmitted to the catheter securement device.

17. The catheter securement device of claim 16, wherein the uplift focus area is located at the distal edge of the retention member.

18. The catheter securement device of claim 17, wherein the uplift focus area is substantially midway between the distal edge and the proximal edge of the base member.

19. The catheter securement device of claim 18, wherein the base member tents up when the force is applied to the plurality of distal tube members.

* * * * *